United States Patent [19]

Tamura et al.

[11] Patent Number: 4,745,209
[45] Date of Patent: May 17, 1988

[54] METHOD OF PREPARING α-ARYLALKANOIC ESTERS

[75] Inventors: Yasumitsu Tamura, Takarazuka; Junichi Haruta, Osaka, both of Japan

[73] Assignee: Yasumitsu Tamura, Japan

[21] Appl. No.: 839,213

[22] Filed: Mar. 13, 1986

[30] Foreign Application Priority Data

Mar. 15, 1985 [JP] Japan ................................ 60-52966

[51] Int. Cl.[4] .......................................... C07C 67/475
[52] U.S. Cl. ...................................... 560/9; 560/19; 560/55; 560/102; 560/105
[58] Field of Search ....................... 560/9, 19, 55, 102, 560/105, 109, 130

[56] References Cited

FOREIGN PATENT DOCUMENTS

| 89711 | 9/1983 | European Pat. Off. |
| 108442 | 5/1984 | European Pat. Off. |
| 59-163345 | 9/1984 | Japan |
| 2042543 | 9/1980 | United Kingdom |

OTHER PUBLICATIONS

Tamura et al., *Synthesis*, pp. 231–232 (Mar. 1984).
C. Giordano et al., *Angew. Chem. Int. Ed. Engl.*, 23, pp. 413–419 (1984).
A. Goosen and C. W. McCleland, *J. Chem. Soc., Chem. Commun.*, pp. 1311–1312 (1982).
Y. Hamada and T. Shioiri, *Tetrahedron Lett.*, 23(2), pp. 235–236.
S. D. Higgins and C. B. Thomas, *J. Chem. Soc., Perkin Trans. I*, pp. 235–242 (1982).
K. Fujii et al., *Synthesis*, pp. 456–457 (1982).
B. Myrboh et al., *Synthesis*, pp. 126–127 (1981).
G. Tsuchihashi et al., *Tetrahedron Lett.*, 22(43), pp. 4305–4308, (1981).
T. Shioiri and N. Kawai, *J. Org. Chem.*, 43(14), pp. 2936–2938 (1978).
A. McKillop et al., *J. Am. Chem. Soc.*, 95(10), pp. 3340–3343 (1973).

*Primary Examiner*—Michael L. Shippen
*Attorney, Agent, or Firm*—Bernard, Rothwell & Brown

[57] ABSTRACT

Alpha-arylalkanoic esters are prepared by reacting a trivalent iodine compound represented by the general formula:

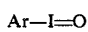

wherein Ar is an aromatic hydrocarbon, group, with a carbonyl compound represented by the general formula

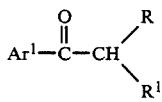

wherein $Ar^1$ is an aromatic hydrocarbon, R is a hydrogen atom or an alkyl group and $R^1$ is a hydrogen atom or an alkyl group, in the presence of an orthocarboxylic ester.

8 Claims, No Drawings

METHOD OF PREPARING α-ARYLALKANOIC ESTERS

TECHNICAL FIELD

The present invention relates to a method of preparing α-arylalkanoic esters.

BACKGROUND OF THE INVENTION

Alpha-arylalkanoic acids are widely used as active anti-inflammatory, analgesic, and anti-pyretic pharmaceutical products. Such acids include, for example, ibuprofen, 2-(4-isobutylphenyl)propionic acid and fenoprofen, 2-(3-phenoxyphenyl)propionic acid. Various methods are known in the art for making these acids and their corresponding esters. For example, α-arylalkanoic esters can be made from corresponding carbonyl compounds of the general formula:

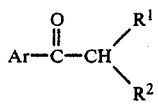

wherein at least one of the $R^1$ and $R^2$ groups is an alkyl group and the other is a hydrogen atom or an alkyl group or wherein $R^1$ is a bromine atom and $R^2$ is an alkyl group (*Journal Am. Chem. Soc.*, 95: 3340 [1973; *Synthesis*, p. 126 [1981]; *Synthesis*, p. 456, [1982]; *Parkin Transactions* (British Chem. Soc.), 1: 235 [1982]; *Tetrahedron Letters*, 23: 235 [1982], *Tetrahedron Letters* 22: 4305 [1981]; *Journal Organic Chemistry*, 43: 2936 [1978]; *Chemical Communications*, p. 1311 [1982]).

Each of the aforementioned methods has at least one disadvantage, such as requiring the use of a poisonous thallium or lead salt or a precious, and expensive, silver salt, requiring a lengthy reaction time, and producing the desired product in low yields.

Laid-Open Japanese Patent Publication No. 163,345 (1984), incorporated herein by reference, teaches a method of preparing α-arylalkanoic esters represented by the general formula

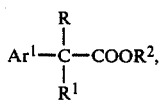

wherein $Ar^1$ is an aromatic hydrocarbon group, R and $R^1$ each represent a hydrogen atom or an alkyl group, and $R^2$ is an alkyl group, by reacting a compound of trivalent iodine having the general formula

wherein Ar is an aromatic hydrocarbon group and X and Y are each a group which can be eliminated as an anion, with a carbonyl compound having the general formula

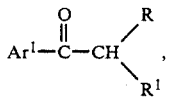

wherein $Ar^1$, R, and $R^1$ are as defined above. The reaction takes place in the presence of an orthocarboxylic ester having the general formula $ZC(OR^2)_3$, wherein $R^2$ is an alkyl group and Z is a hydrogen atom or an alkyl group. Although this method eliminates several disadvantages of methods taught by the prior art, it employs a relatively expensive trivalent iodine compound which may show signs of instability depending upon the groups selected as X and Y. Accordingly, further improvements are sought.

It thus is an object of the present invention to develop an economical method of preparing α-arylalkanoic ester compounds that is not hindered by the disadvantages of methods known in the art. Other objects of the present invention will become apparent by reading the description of the present invention contained herein.

SUMMARY OF THE INVENTION

In accordance with the present invention, α-arylalkanoic esters of the general formula

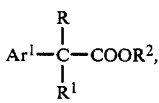

wherein $Ar^1$ is an aromatic hydrocarbon group, R is a hydrogen atom or alkyl group, $R^1$ is a hydrogen atom or alkyl group and $R^2$ is an alkyl group, are prepared by reacting a trivalent iodine compound represented by the general formula:

wherein Ar is an aromatic hydrocarbon group, with a carbonyl compound represented by the general formula

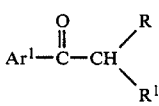

wherein $Ar^1$ is an aromatic hydrocarbon, R is a hydrogen atom or an alkyl group and $R^1$ is a hydrogen atom or an alkyl group, in the presence of an orthocarboxylic ester represented by the general formula $ZC(OR^2)_3$, wherein $R^2$ is an alkyl group and Z is a hydrogen atom or an alkyl group.

DETAILED DESCRIPTION OF THE INVENTION

The present invention relates to a method of preparing α-arylalkanoic esters. In accordance with this method, the α-arylalknoic esters are prepared by reacting a trivalent iodine compound with a carbonyl compound in the presence of an orthocarboxylic ester. Applicants have discovered that the α-arylalkanoic esters can be obtained in high yields by a simple reaction procedure using an inexpensive and nonpoisonous trivalent iodine compound of the general formula Ar—I═O, wherein Ar is an aromatic hydrocarbon.

By the methods of this invention, α-arylalkanoic esters represented by the general formula

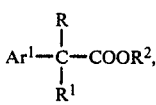

where $Ar^1$ is an aromatic hydrocarbon, R is a hydrogen atom or an alkyl group, $R^1$ is a hydrogen atom or an alkyl group, and $R^2$ is an alkyl group, are prepared by reacting a trivalent-iodine compound represented by the general formula:

wherein Ar is an aromatic hydrocarbon, with a carbonyl compound represented by the general formula:

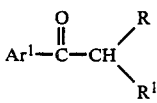

where $Ar^1$, R and $R^1$ are the same as defined above, in the presence of an orthocarboxylic ester represented by the general formula $ZC(OR^2)_3$, wherein $R^2$ is an alkyl group and Z is a hydrogen atom or an alkyl group.

The trivalent iodine compound can be prepared in accordance with conventional methods known to persons skilled in the art. For example, the compound can be prepared by making a dichloro trivalent iodine compound of the formula

by reacting an iodinated aromatic hydrocarbon, Ar-I, with chlorine, then reacting the resultant dichlorocompound with an aqueous alkali oxide solution (Lucas, H. J., et al., *Organic Syntheses* 3: 483 [1954]). The trivalent iodine compound also can be prepared by directly oxidizing an iodinated aromatic hydrocarbon with various oxidation agents. Known direct oxidizing methods include those where the oxidizing agent is fuming nitric acid (Meyer, V. et al. *Ber* 25: 2632 [1892]), potassium permanganate (Asknasy, P., et al. *Ber* 26: 1354 [1893]), ozone (Harries, C. *Ber* 36: 2996 [1903]) and potassium persulfate (Kennedy, R. J., et al. *J. Org. Chem.* 25: 1901[1960]).

An advantage to using these trivalent iodine compounds is that as the reaction of the invention progresses, iodide compounds Ar—I are produced from the trivalent iodic compounds. The Ar—I compounds can be regenerated and converted back into the Ar—I=O compounds, thus reducing the costs of the reaction.

In the formula representing the trivalent iodine compound, Ar is an aromatic hydrocarbon which optionally carries a substituent on the aromatic ring. The substituent may be a linear or branched alkyl group such as methyl, ethyl, n- or iso-propyl, or n-, iso-, sec- or t-butyl group; an alkoxy group such as methoxy, ethoxy, n- or iso-propyloxy, or n-, iso-, sec- or t-butoxy group; an aryloxy group such as phenoxy; an acyloxy group such as acetoxy, n- or iso-propionyloxy, n-, iso-, sec- or t-butyloyloxy, or benzoyloxy group; or an electron attractive group such as a nitro, acetyl, propyl, benzoyl, nitrile or sulfonyl group.

In the carbonyl compound, the other reactant, $Ar^1$ also represents an aromatic hydrocarbon group which optionally may carry a substituent on the aromatic ring. The substituent may be a saturated hydrocarbon group such as an alkyl group having 1 to about 4 carbon atoms; an unsaturated aliphatic hydrocarbon group such as vinyl, ethynyl, or alyl group, an alkenyl or alkenyloxy group having such an unsaturated group; an alkoxy group such as methoxy, ethoxy, n- or iso-propyloxy, or n-, iso-, sec-, or t-butyloxy; a phenoxy group, an aliphatic acyloxy group, or a benzoyloxy group; an alkylthio group such as methylthio, ethylthio, n- or iso-propylthio, or n-, sec-, iso- or t-butylthio group; an arylthio group such as phenylthio; an aryl group, such as phenyl; a halogen atom; or an amino group which is mono- or di-substituted by n- or iso-propyl, or n-, iso-, sec- or t-butyl group.

The groups R and $R^1$ may each independently represent an alkyl group, such as methyl, ethyl or propyl, or a hydrogen atom.

Preferably, the carbonyl compound is an acetophenone or propiophenone, the phenyl group of which optionally is substituted with an alkyl group, halogen or alkoxy group.

Desirably, the molar ratio of trivalent iodine compound to carbonyl compound in the reaction is at least 1:1.

The reaction is carried out in the presence of an orthocarboxylic ester represented by the general formula $ZC(OR^2)_3$. In this formula Z is a hydrogen atom or an alkyl group and $R^2$ is an alkyl group. Preferably, the compound is the methyl, ethyl or propyl ester of orthoformic acid. Ethyl orthoformate is especially preferred in comparison to other orthocarboxylic esters in that it is the most economical.

To obtain the desired α-arylalkanoic esters, the trivalent iodine compound and carbonyl compound are reacted together in the presence of the orthocarboxylic ester with the addition of an acid, such as concentrated sulfuric acid or perchloric acid. The reaction can be carried out at room temperature or heat may be applied to raise the reaction temperature up to about 80° C.

The reaction can be carried out in the absence of a solvent, or, if desired, in the presence of a solvent selected from the group consisting of hydrocarbons, halogenated hydrocarbons, lower aliphatic esters, lower aliphatic ethers, lower aliphatic nitriles, lower aliphatic alcohols, lower aliphatic acids and nitroparaffin. These solvents include, for example, linear or cyclic halogenated hydrocarbons having 1 to about 6 carbon atoms, such as chloroform, dichloromethane and chlorobenzene; lower alkylesters such as methyl, ethyl and propyl esters of a fatty acid having 1 to about 3 carbon atoms, such as formic acid, acetic acid and propionic acid; lower aliphatic ethers having about 2 to about 4 carbon atoms such as dimethyl ether, diethyl ether and methyl ethyl ether; lower aliphatic nitriles, such as acetonitrile and propionitrile; lower aliphatic alcohols having 1 to about 4 carbon atoms, including methanol, ethanol, n- or iso-propanol, or t-butanol; lower fatty acids having 1 to about 3 carbon atoms, i.e., formic acid, acetic acid and propionic acid; and nitroparaffin having 1 to about 2 carbon atoms, such as nitromethane and nitroethane. It has been found that when the reaction is conducted in the presence of a solvent selected from this group, significantly less orthocarboxylic ester is needed than when the reaction is carried out in the absence of such a solvent. As the orthocarboxylic ester can be an expensive component of the reaction process, conducting the reaction in the presence of the solvent can decrease the cost of producing the α-arylalkanoic esters.

The solvents may be used singly or as a mixture of two or more. If solvent recovery is taken into consideration, use of a single solvent may be preferable for ease of recovery of the reaction product.

Reaction times can be determined by checking for the presence (or absence) of the carbonyl compound in the reaction mixture by thin layer chomatography (TLC) in accordance with conventional methods. The α-arylalkanoic esters produced by the method of this invention can be recovered by conventional methods from the reaction mixture.

The following examples are provided for illustrative purposes and are not to be construed as limiting.

EXAMPLE 1

One millimol (134) mg of propiophenone and 1.2 millimole (264 mg) of iodosobenzene were stirred in 4 ml of methyl orthoformate in the presence of 2 millimol (196 mg) of concentrated $H_2SO_4$ at room temperature for 2 hours. The resultant solution obtained was extracted with ether and the extractant was washed with water, dried with anhydrous magnesium sulfate, and then the solvent was distilled off. The residue was purified with silicagel column chromatography (benzene). There was obtained 143 mg of methyl α-phenylpropionate (a yield of 87%) having the following analytical characteristics:

$IR\nu_{max}^{CHCl3}$ cm$^{-1}$: 1730.
$^1$H-NMR(CDCl$_3$)δ: 1.48 (d, J=7 Hz, 3H); 3.62 (s, 3H); 3.70 (q, J=7 HZ, 1H); 7.24 (s, 5H).

EXAMPLE 2

The procedure of Example 1 was followed with the exception that ethyl orthoformate was used in place of methylorthoformate. The reaction yielded 143 mg of ethyl α-phenylpropionate (a yield of about 83%). The product had the following characteristics:

$IR\nu_{max}^{CHCl3}$ cm$^{-1}$: 1725.
$^1$H-NMR(CDCl$_3$)δ: 1.21 (t, J=7 Hz, 3H); 1.48 (d, J=7 Hz, 3H); 3.68 (q, J=7 HZ, 1H); 4.10 (q, J=7 Hz, 2H); 7.26 (S, 5H).

EXAMPLES 3-7

The procedure of Example 1 was repeated with the exception that various aryl ethyl ketones of the general formula

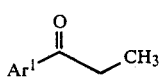

(the aryl portions are illustrated in Table 1 below) were used in place of the propiophenone. The reaction time was controlled depending upon the ketone used. The results are shown in Table 1.

TABLE 1

| Example No. | Ar | Reaction Time Hour | Product Yield (%) |
|---|---|---|---|
| 3 | 4-CH$_3$-C$_6$H$_4$- | 2 | 84 |
| 4 | 4-iPr-CH$_2$-C$_6$H$_4$- | 2 | 85 |
| 5 | 4-MeO-C$_6$H$_4$- | 1 | 82 |
| 6 | 4-Br-C$_6$H$_4$- | 6 | 78 |
| 7 | 4-PhS-C$_6$H$_4$- | 5 | 80 |

EXAMPLE 8-12

The procedure of Example 1 was repeated with the exception that various aryl methyl ketones of the general formula

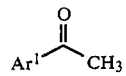

(the Ar$^1$ groups are defined in column 2 of Table 2) were used in place of propiophenone. The reactions were carried out at 50° C.; the reaction times were controlled and varied depending upon the particular ketone used. The results are shown in Table 2.

TABLE 2

| Example No. | Ar | Reaction Time Hour | Product Yield (%) |
|---|---|---|---|
| 8 | C$_6$H$_5$- | 2 | 71 |
| 9 | 4-CH$_3$-C$_6$H$_4$- | 2 | 70 |
| 10 | 4-iPr-CH$_2$-C$_6$H$_4$- | 2 | 62 |

TABLE 2-continued

| Example No. | Ar | Reaction Time Hour | Product Yield (%) |
|---|---|---|---|
| 11 | 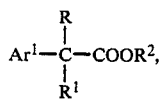 | 1 | 68 |
| 12 | 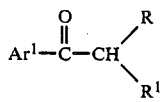 | 4 | 48 |

EXAMPLE 13

The procedure of Example 1 was followed with the exception that 2 ml. of methyl orthoformate were used and 2 ml. of chloroform were added as a solvent. The reaction produced 128 mg. of methyl α-phenyl propionate, a yield of 78%.

EXAMPLE 14

The procedure of Example 1 was followed with the exception that 1 ml. of ethyl orthoformate was used and 3 ml. of ethyl acetate were added as a reaction solvent. The reaction time was 3 hours. The reaction produced 144 mg. of ethyl α-phenyl propionate, a yield of 81%.

We claim:

1. A method for preparing an α-arylalkanoic ester represented by the general formula $$Ar^1-\underset{R^1}{\overset{R}{\underset{|}{C}}}-COOR^2,$$

wherein $Ar^1$ is an aromtic hydrocarbon, R is an alkyl group or a hydrogen atom, $R^1$ is an alkyl group or a hydrogen atom, and $R^2$ is an alkyl group, which comprises reacting, under α-arylalkanoic ester-producing conditions, a trivalent iodine compound represented by the general formula $$Ar-I=O$$

wherein Ar is an aromatic hydrocarbon, with a carbonyl compound represented by the general formula $$Ar^1-\underset{}{\overset{O}{\underset{\|}{C}}}-CH\underset{R^1}{\overset{R}{\diagup}}$$

wherein $Ar^1$, R and $R^1$ are as defined above, in the presence of an orthocarboxylic ester represented by the general formula $$ZC(OR^2)_3$$

wherein Z is an alkyl group or a hydrogen atom and $R^2$ is as defined above.

2. The method of claim 1 wherein Ar is a phenyl group which is optionally substituted by an alkyl, alkoxy, aryloxy; acyloxy or electron attractive group; and $Ar^1$ is a phenyl group which is optionally substituted by a saturated or unsaturated hydrocarbon, aryl, alkoxy, alkenyloxy, benzoyloxy, phenoxy, aliphatic acyloxy, alkynyloxy, alkylthio, arylthio, substituted amino group or a halogen atom, and R and $R^1$ are each a hydrogen atom or an alkyl group comprising one to three carbon atoms.

3. A method as claimed in claim 1 or 2 where Ar is a phenyl group which is optionally substituted by an alkyl group having 1 to 4 carbon atoms, an alkoxy group having 1 to 4 carbon atoms, a phenyloxy group, an acyloxy group having 1 to 4 carbon atoms, or a nitro, acyl, cyano, or sulfonyl group; Ar' is a phenyl group which is optionally substituted by an alkyl group having 1 to 4 carbon atoms, a phenyl group, an ethynyl group, an alkoxy group having 1 to 4 carbon atoms, a phenoxy group, an aliphatic acyloxy group, benzoyloxy group, alkylthio group having 1 to 4 carbon atoms, an arylthio group, a mono- or di-substituted alkyl amino group or a halogen atom; and R and R' each comprises a hydrogen atom or an alkyl group having 1 to 3 carbon atoms.

4. The method of claim 1 wherein said orthocarboxylic ester is methyl orthoformate, ethyl orthoformate, or propyl orthoformte.

5. The method of claim 1 wherein said trivalent iodine compound and said carbonyl compound are reacted in the presence of said orthocarboxylic ester in the presence of at least one solvent selected from the group consisting of hydrocarbons, halogenated hydrocarbons, lower alihatic esters, lower aliphatic ethers, lower aliphatic alcohols, lower aliphatic nitriles, lower aliphatic acids and nitroparaffin.

6. The method of claim 5 wherein said solvent or solvents is selected from the group consisting of a linear or cyclic hydrocarbon having 5 to 7 carbon atoms; a linear or cyclic halogenated hydrocarbon having 1 to 6 carbon atoms; methyl, ethyl, n- or isopropyl ester of a fatty acid having 1 to 3 carbon atoms; an aliphatic ether having 2 to 4 carbon atoms, an alkyl cyanide having 1 to 2 carbon atoms, an aliphatic alcohol having 1 to 4 carbon atoms, a fatty acid having 1 to 3 carbon atoms and nitrated paraffin having 1 to 2 carbon atoms.

7. The method of claim 1 wherein the molar ratio of trivalent iodine compound to carbonyl compound is at least 1:1.

8. The method of claim 1 wherein the reaction is conducted at room temperature in the presence of concentrated sulfuric acid.

* * * * *